US00RE38145E

(19) United States
(12) Reissued Patent
Lynn

(10) Patent Number: US RE38,145 E
(45) Date of Reissued Patent: Jun. 17, 2003

(54) LUER-RECEIVING MEDICAL VALVE

(76) Inventor: Lawrence A. Lynn, 862 Curleys Ct., Worthington, OH (US) 43235

(21) Appl. No.: 09/480,452

(22) Filed: Jan. 11, 2000

Related U.S. Patent Documents

Reissue of:
(64) Patent No.: 5,474,544
Issued: Dec. 12, 1995
Appl. No.: 08/345,808
Filed: Nov. 22, 1994

U.S. Applications:

(63) Continuation-in-part of application No. 08/248,646, filed on May 25, 1994, now Pat. No. 5,549,651.

(51) Int. Cl.[7] ..... A61M 25/16
(52) U.S. Cl. ..... 604/537; 128/912; 251/349
(58) Field of Search ..... 604/533, 537, 604/538, 539, 288.01, 288.03, 247, 256, 236, 237, 167.01, 167.02, 167.04; 251/149.1, 149.3, 349, 354; 128/912

(56) References Cited

U.S. PATENT DOCUMENTS

| | | | | | |
|---|---|---|---|---|---|
| 3,659,587 | A | * | 5/1972 | Baldwin | 604/237 |
| 3,986,508 | A | * | 10/1976 | Barrington | 604/905 |
| 4,197,848 | A | * | 4/1980 | Garrett et al. | 604/19 |
| 4,214,779 | A | * | 7/1980 | Losell | 604/86 |
| 4,496,350 | A | * | 1/1985 | Cosentino | 604/175 |
| 4,511,359 | A | * | 4/1985 | Vaillancourt | 604/905 |
| 4,758,225 | A | * | 7/1988 | Cox et al. | 604/167.03 |
| 4,763,648 | A | * | 8/1988 | Wyatt | 600/486 |
| 4,768,568 | A | * | 9/1988 | Fournier et al. | 604/411 |
| 4,834,152 | A | * | 5/1989 | Howson et al. | 604/411 |
| 4,929,235 | A | * | 5/1990 | Merry et al. | 604/167.04 |
| 4,950,257 | A | * | 8/1990 | Hibbs et al. | 604/264 |
| 4,981,469 | A | * | 1/1991 | Whitehouse et al. | 604/905 |
| 4,998,927 | A | * | 3/1991 | Vaillancourt | 604/411 |
| 5,108,380 | A | * | 4/1992 | Herlitze et al. | 604/167.04 |
| 5,147,305 | A | * | 9/1992 | Nakamura et al. | 604/110 |
| 5,149,327 | A | * | 9/1992 | Oshiyama | 251/149.1 |
| 5,201,725 | A | * | 4/1993 | Kling | 604/284 |
| 5,211,370 | A | * | 5/1993 | Powers | 251/212 |
| 5,215,537 | A | * | 6/1993 | Lynn et al. | 215/249 |
| 5,215,538 | A | * | 6/1993 | Larkin | 137/516.13 |
| 5,242,432 | A | * | 9/1993 | DeFrank | 604/247 |
| 5,251,873 | A | * | 10/1993 | Atkinson et al. | 251/149.1 |
| 5,273,533 | A | * | 12/1993 | Bonaldo | 604/905 |
| 5,322,518 | A | * | 6/1994 | Schneider et al. | 604/167.03 |
| 5,360,413 | A | * | 11/1994 | Leason et al. | 137/843 |

FOREIGN PATENT DOCUMENTS

WO 90/11103 * 10/1990

OTHER PUBLICATIONS

Brochure by McGaw, The Clave.™ IV Administration System.*
Sample of Buron One–Way Valve System.*

* cited by examiner

*Primary Examiner*—Anhtuan T. Nguyen
(74) *Attorney, Agent, or Firm*—Nixon & Vanderhye PC

(57) ABSTRACT

A luer receiving medical valve for the sterile transfer of fluid from a luer-tapered male end having a surrounding female luer lock threaded end. The luer receiver includes a housing having an inlet and an outlet and a lumen extending from the inlet to the outlet. An elastomeric sealing member occludes the inlet and has a slit extending through it. In a preferred embodiment, a support is provided adjacent the housing inlet and adjacent the sealing member. The support includes opposing posts separated by slots, the slots permitting expansion of the sealing member when the male luer is inserted into the slit.

47 Claims, 10 Drawing Sheets

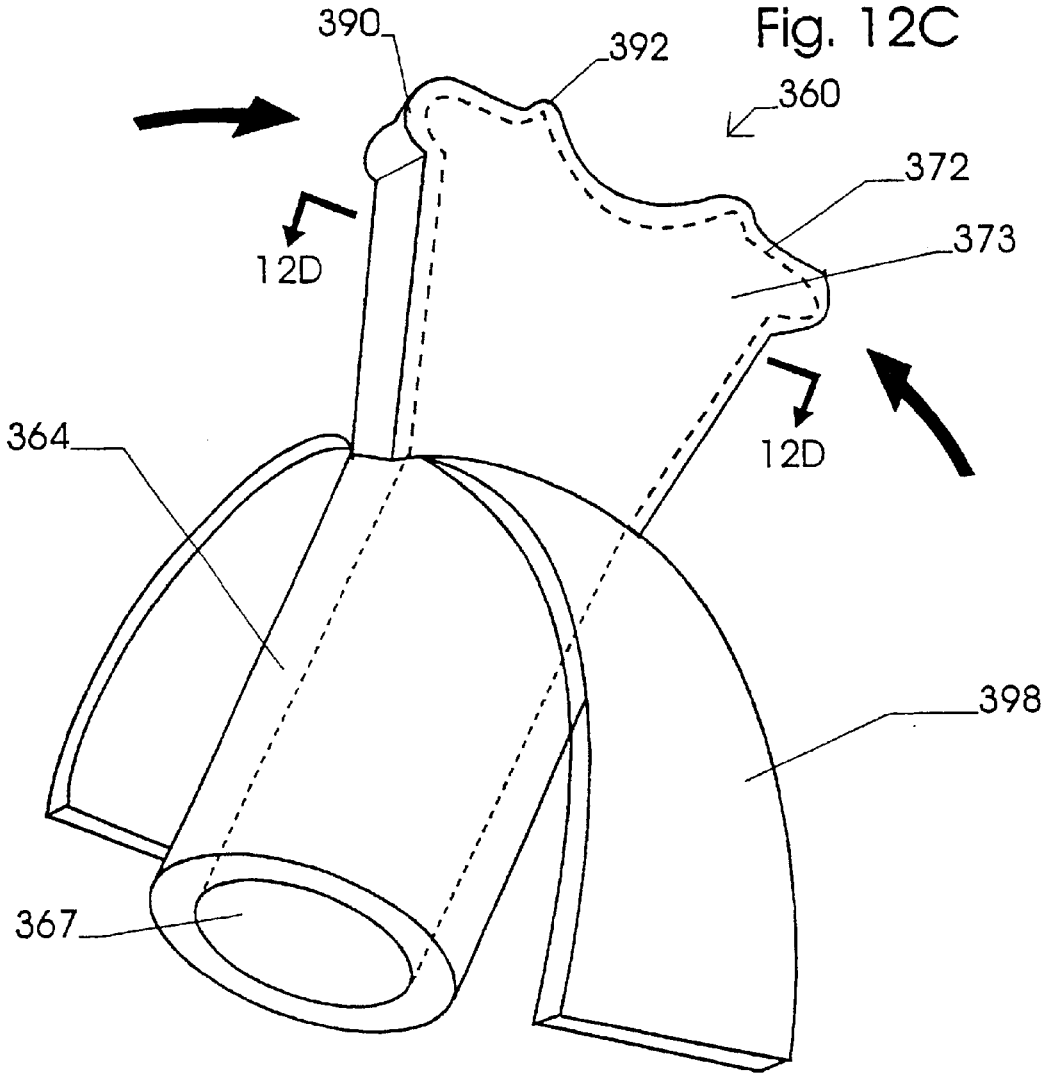
Fig. 12C
Fig. 12D
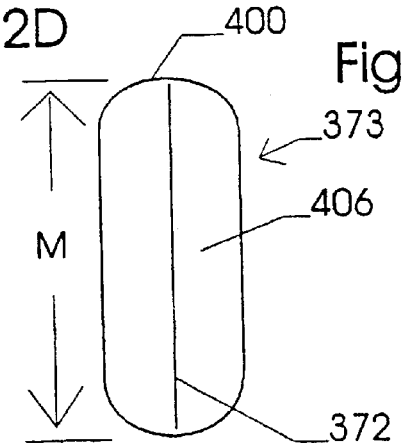
Fig. 12E
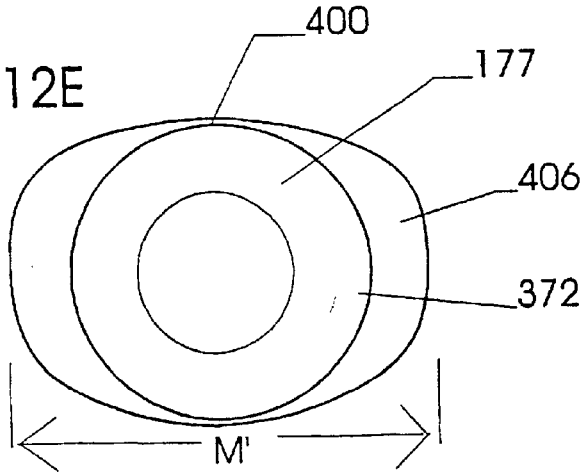

LUER-RECEIVING MEDICAL VALVE

Matter enclosed in heavy brackets [ ] appears in the original patent but forms no part of this reissue specification; matter printed in italics indicates the additions made by reissue.

FIELD OF THE INVENTION

This is a continuation-in-part of application Ser. No. #08/248,646, filed May 25, 1994 (the disclosure of which is hereby incorporated by reference as if completely disclosed herein). This invention relates to the safe and sterile transfer of medical fluid, in particular intravenous fluid and to the sampling of blood as from indwelling arterial and venous catheters and the like. The invention particularly relates to the administration of intravenous fluid or pharmaceuticals to a patient. The background and: problems associated with fluid and drug administration and with blood sampling are extensively discussed in my U.S. Pat. No. 4,838,855, Blood Aspiration Assembly and Method, issued Jun. 13, 1990; U.S. Pat. No. 5,178,607, Blood Aspiration Assembly Septum and Blunt Needle Aspirator, issued Jan. 12, 1993; U.S. Pat. No. 5,137,524, Universal Intravenous Connector with Dual Catches, issued Aug. 11, 1992; U.S. Pat. No. 4,946,445, Intravenous Line Coupling Device, issued Aug. 7, 1990; U.S. Pat. No. 5,215,537, Septum for a Blunt Cannula, issued Jun. 1, 1993; and U.S. Pat. No. 5,167,643, Needle Protection Station, issued Dec. 1, 1992 (the disclosure of each of these patents is hereby incorporated by reference as if completely disclosed herein). These patents provide additional background for the present invention.

BACKGROUND AND SUMMARY OF THE INVENTION

The risk of needlestick injury and the expense associated with accessory cannulae, whether blunt or sharp, are well known. Conventional intravenous tubing systems utilize tapering luer male cannula connectors, often within an associated surrounding threadable member defining a luer-lock connector commonly used for achieving tight, sustained connections. A bare luer taper cannula without the associated threadable member is commonly called a luer slip connector and is widely utilized for brief prn injections. Both of these luer systems are in wide use throughout conventional hospital systems and it would be preferable to develop a connecting valve system which receives and is activated by conventional luer slip tapers or luer lock tapers so that incorporation into existing hospital systems is rapid and associated with minimal cost. It would be advantageous for such systems to avoid deadspace so that the surface could be easily wiped with antiseptic to avoid the need for capping after each use. Furthermore, the elimination of deadspace allows for the aspiration of blood through such systems without the collection of blood within the deadspace. Another important feature of such systems is the minimization of "kickback"—that is, it is important that the luer slip tip or luer lock systems, when not tightly locked, do not kickback out of the valve, thereby producing the potential for a spurt of blood or fluid into the environment and potential contamination of the operator.

The prior art includes several luer-receiving valves which do not have substantial deadspace. U.S. Pat. No. 5,201,725 shows a valve which utilizes an elastomeric member which opens by force induced by a threadable member over the elastomeric septum piston. Such a system will not work with a conventional luer lock system since the role taper extends centrally adjacent the luer lock threading member and therefore, it would not be possible to compress the septum piston within the luer-lock threads in such a system without inserting the male member itself into the septran piston. The background discussed in the aforementioned patent provides additional background for the present invention.

A device, designated the CLAVE™, for an injection port marketed by McGaw, is included in the Prior Art. This device utilizes a cannula surrounded by a septum piston. The septum piston is compressed by the luer taper, thereby allowing the needle and its associated bore to enter the bore of the luer taper, thereby opening fluid communication. However, such systems would be expected to be associated with substantial kickback when used with a luer slip system since the septum piston must be relatively resilient to prevent leakage associated with higher fluid pressures within the cannula. Further, tile requirement of a spike or cannula within the bore of the valve results in considerable increase in expense associated with complex insert molding of the device. It is, therefore, preferable to develop a more simplified valve system which can receive a luer taper cannula and which eliminates the need for complex insert molding to minimize the potential for kickback and the potential for trapped fluid or blood while still providing a deadspace-free surface which can be easily wiped with antiseptic. Such a device also will not receive a blunt cannulae and, therefore, may be difficult to implement with conventional drug delivery systems.

In general, the present invention comprises a housing including a main conduit having a main bore and further having a branch extending away from the main conduit and including a secondary bore extending through the branch in fluid communication with the main conduit. The secondary bore may be aligned directly with the main conduit or may branch from the main conduit. The main conduit may, for example, comprise a catheter or may be a primary intravenous tubing system or arterial line. The secondary bore defines a longitudinal axis. An elastomeric septum piston is disposed within the secondary bore and at least a portion of the elastomeric septum piston is moveable by either compression or by longitudinal advancement along the secondary bore toward the main bore. In one preferred embodiment, the septum piston is cylindrical and includes a centrally positional slit extending along the longitudinal axis of the cylindrical septum piston. The cylinder includes a proximal end and a distal end. The proximal end preferably extends to a position adjacent the proximal end of the secondary bore so that the surface of the proximal end of the septum piston is easily accessible adjacent the proximal end of the branch and therefore can be easily wiped with antiseptic. This is an important feature since it eliminates the need for capping after blood aspiration or drug injection. The bore of the secondary branch preferably includes two opposing projecting members along a distal portion of the bore which effectively narrow the diameter of the bore along at least a portion of one longitudinal axis. In the preferred embodiment, the central slit through the septum piston defines a longitudinal axis transverse to the longitudinal axis of the septum piston. With this embodiment, the longitudinal plane of the narrowed distal portion of the secondary bore is aligned with the longitudinal axis of the slit through the elastomeric septum piston. Furthermore, the elastomeric septum piston is sized to be transversely compressed by the projecting distal portions of the secondary bore. Since the slit is aligned with the projecting portions, transverse compression of the septum piston occurs along an axis which corresponds with the longitudinal axis of the slit so that when the elastomeric member is pushed from a proximal position into a distal position, the elastomeric member is transversely compressed by the projecting portions along the distal secondary bore, the compression causing the formerly tightly-closed slit to shorten and thereby open, allowing fluid to pass through a nascent flow channel formed by the shortened slit through the elastomeric septum piston. When the septum piston retracts away from the distal portion back into the proximal portion, the slit returns to its tightly closed position, thereby occluding further fluid communication through the septum piston.

In the preferred embodiment, the projecting portions progressively lengthen to define a progressively decreasing distance between the projecting members so that the projecting members are closer to one another adjacent the main bore than adjacent the proximal cylindrical portion of the secondary bore. This effectuates a progressive enlargement of the opening through slit of the elastomeric septum piston when the elastomeric septum piston is fully advanced into the proximal portion of the secondary bore. Furthermore, after removal of the luer, as the elastomeric septum piston retracts away from the distal compressing portion toward the proximal portion, the slit progressively closes from its proximal extent toward its distal extent, thereby expressing fluid toward the main bore rather than toward the proximal opening of the secondary bore. This reduces the chance of blood or fluid refluxing out of the septum piston into the environment or into the secondary bore when luer taper cannula is withdrawn from the secondary bore.

The septum piston can include a proximal extension which can be cylindrical and can be integral with the septum piston and can be formed of like elastomeric material such as silicone or latex rubber. The septum piston and the extension can be formed together as a single integral flexible conduit having an interior sterile enclosed flow path. In one embodiment, the proximal end of the conduit is closed to comprise the septum piston having a sealed perforation, as described above;the distal end of the conduit is opened and engages a seat which can provide a seal. The conduit therefore provides an enclosed flow path from the luer tip through the conduit when the closed end of the conduit is distorted such that the perforation is open. The distal open end of the conduit can be intussuscepted over a tube which can be rigid so as to provide a fixed sealed seat. Alternatively, the seat can be provided by a slot formed within an outer housing. An advantage of the tubular seat is that it provides easy mounting of the tubular flexible conduit during manufacture and further can provide an effective seal against contamination of the interior flow path within the flexible conduit during operation. It is considered potentially advantageous to provide an enclosed sterile central flow path which does not contact the housing to thereby minimize the potential for contact contamination of the flow path.

It can be seen that the flexible conduit in conjunction with the seat can provide both a sealed interior flow path and can further provide an additional elastic spring force when mounted with the rigid seat such that longitudinal force applied by insertion of the luer to the closed end of the conduit results in either longitudinal compression or folding of the tubular conduit which will then rebound to its original position when the longitudinal force applied by the luer tip is removed. Since the flow path need not engage the housing, the housing can be provided as only an incomplete cylinder or can be provided as linear support struts, thereby increasing visibility of the flexible conduit and fluid path and allowing more open access to the tabular seat for more easy molding and mounting of the flexible tubular conduit with the seat during manufacture.

In one embodiment, the proximal face of the septum piston of the tubular conduit is soft such that the face will mold with the distal tip of the luer when the luer tip is advanced against the face, thereby providing enhanced sealing of the luer with the face. The face can also include a circumferential membranous apron extending lateral to the face and over the distal end of the housing of the branch. The apron can then be deflected inwardly by the housing as the septum piston is advanced, thereby providing an additional circumferential seal for the luer tip. The rigid tube can be provided as a wedge or tapered cone member to assist in distorting the septum piston perforation into the open position.

A flow deflector or ramp can be provided when the housing of the branch is mounted to a tubing system to form a secondary branch, as in a T or Y configuration. The flow deflector can ramp flow into deadspace within the flexible conduit or rigid tubular seat so as to minimize the trapping of air bubbles or blood within the seat or flexible conduit when the device is used in blood sampling configurations, such as with arterial lines.

The branch of the main conduit can be aligned directly with or perpendicular to the main conduit or can be at an oblique or acute angle with the main conduit. The main conduit is generally discussed below as integral with the valve, but the main conduit may be a separate piece and sold separately, and may be joined with the branch or the aligned secondary bore by a threadable member as, for example, joining a conventional heparin well or prn adapter to a catheter, stopcock, or IV tubing system.

The branch preferably includes at least one external thread or thread receiver for receiving an internal female threading member to allow a secure threaded connection with a conventional luer-lock type connector of the type commonly used with conventional syringes or intravenous tubing systems.

The use of this luer-activated valve in association with IV piggyback administration generally would require the recapping of the luer taper after use so that the luer taper remains sterile between IV piggyback mediation administrations. My U.S. Pat. No. 5,167,643 (the disclosure of which is hereby incorporated by reference as if completely disclosed herein) describes a Docking Station for receiving a blunt cannula such as a tapered luer end to maintain the sterility of the tapered end. The present invention includes the secondary tubing system having a docking station intended for use with a conventional luer taper cannula of the slip tip or luer lock type. This station utilizes a simple membranous cover since the primary function of the cover is to cover and seal the luer within the station, as discussed in the previous patent. The new protection station may include an annular shield for protecting the fingertips against inadvertent contact of the luer taper since the luer taper has been removed from fluid connection with the patient's blood vessel and, therefore, could be contaminated by potentially infectious material which, by even surface contamination of a nurses fingers, could subsequently enter a fissure in the fingers or otherwise be transferred to a mucous membrane where infection could ensue. The station preferably includes a connecting portion for connecting to a proximal portion of the intravenous piggyback system or supporting pole, as described in my aforementioned patent. The combination of a primary fluid system which incorporates a luer-activated valve and a secondary system which incorporates a luer cannula protection station which protects the tapered blunt cannula of the luer provides reliable intermittent connection to the patient with assurance that the luer taper remains sterile between use and eliminates the need for the utilization of multiple caps, thereby reducing overall cost.

It is the purpose of the present invention to provide an inexpensive medical valve which can be activated by a conventional luer taper cannula and thereby be widely implemented within existing hospital systems.

It is further the purpose of the invention to provide a valve with a central sealed flow path through a flexible conduit, thereby minimizing the potential for contamination of the flow path and allowing for insertion of conventional blunt cannulae.

It is further the purpose of this invention to provide a medical valve which can be easily wiped with antiseptic to eliminate the need for recapping after use. It is further the purpose of this invention to provide a medical valve having substantially no deadspace adjacent its proximal portion to eliminate the pooling of blood or liquid within the valve so that the valve may be repetitively used for the aspiration of blood and reinjection of liquids.

It is further the purpose of this invention to provide a luer-activated opening of a central fluid path which is automatically aligned with the bore of the luer and which will directly communicate with the bore of a luer taper cannula upon the transmission of longitudinal force of the luer taper cannula against the septum piston, thereby providing a mechanism for the opening of a centrally-positioned fluid path at the same time tight sealing occurs adjacent the distal end of the luer taper cannula against the septum piston. It is further the purpose of this invention to provide a valve which progressively closes from its proximal extent to its distal extent, thereby expressing residual fluid from the valve away from the environment. It is further the purpose of this invention to provide a two-piece valve which can be simply manufactured by the insertion of an elastomeric septum piston into a rigid tubular structure, thereby avoiding the need for expensive and complex insert molding.

These and other features will become evident from the summary and detailed description described below. Furthermore, these and other objects and advantages of the invention will be further set forth in the description which follows and, in pan, will be learned from the description or may be learned by practice of the invention. The objects and advantages of the invention may be realized by means of the instrumentalities and combinations particularly pointed out in the appended claims.

BRIEF DESCRIPTION OF THE DRAWINGS

FIG. 12C is a perspective view of the flexible tubular container without the proximal apron.

FIG. 12D is a partial top view through sections 8D—8D of FIG. 12C, showing the relationship of the longitudinal slit to the walls of the septum.

FIG. 12E is a partial section view, according to 12D, showing the luer taper received into the slit.

DESCRIPTION OF THE PRESENTLY PREFERRED EMBODIMENTS

Figure 1:
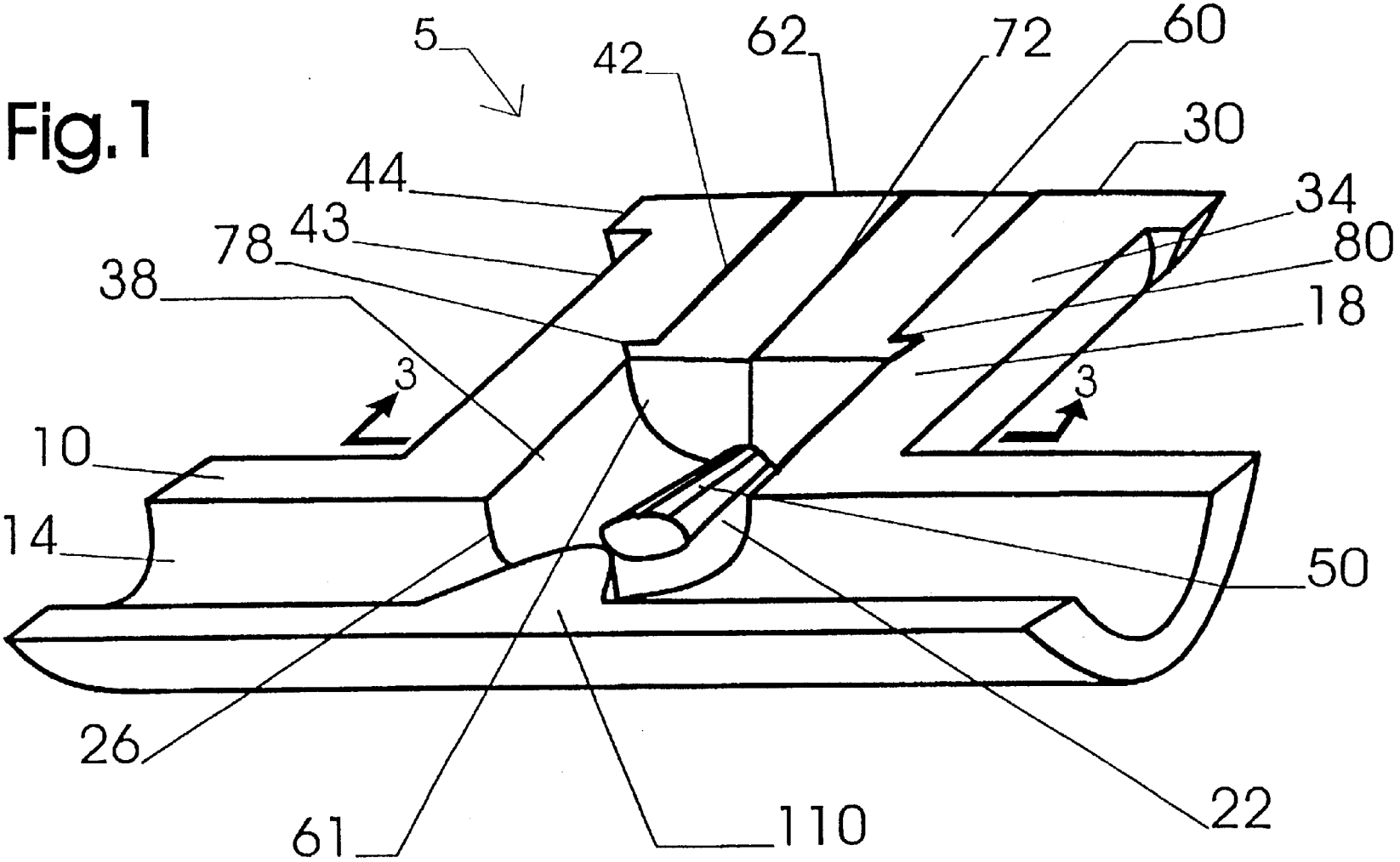
FIG. 1 is a partial perspective view of a longitudinal section of the luer-receiving valve with the piston septum being in its resting detented position.
Figure 2:
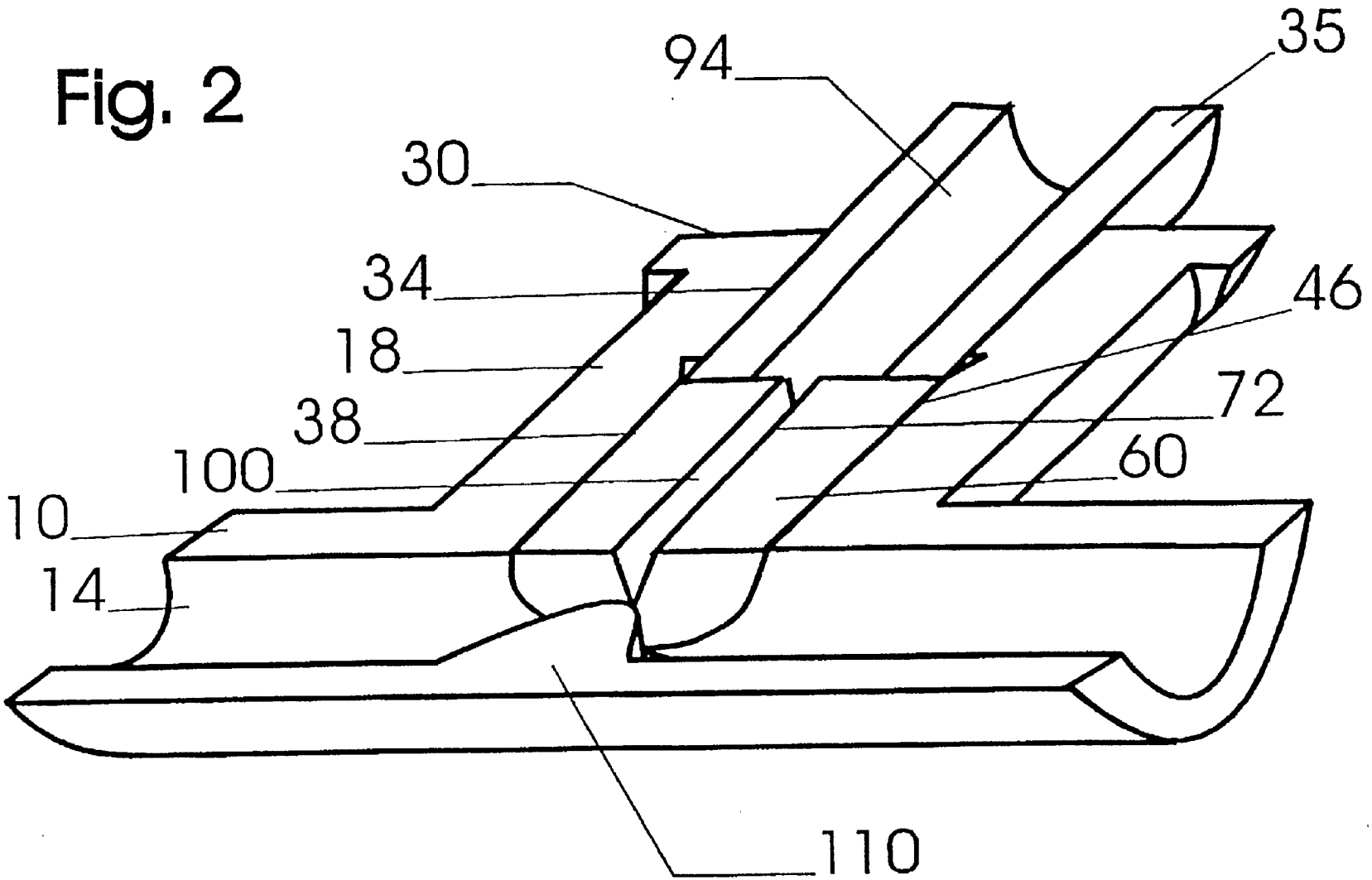
FIG. 2 is a partial perspective view of a longitudinal section of the luer-receiving valve with the blunt luer taper cannula of the conventional slip-tip type fully inserted into the cylinder.
Figure 3:
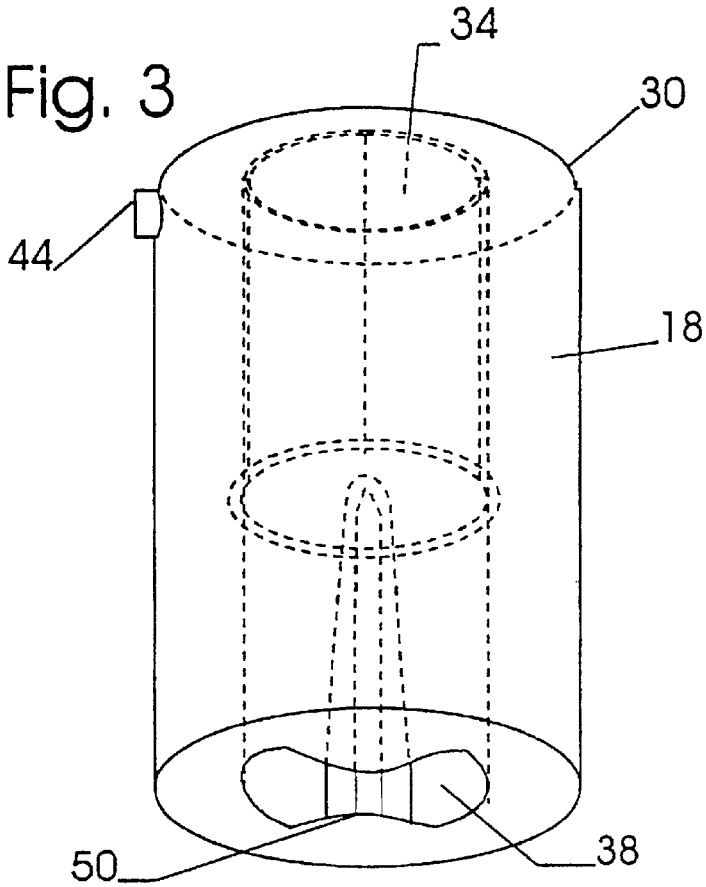
FIG. 3 is a perspective view of a section through lines 3—3 of FIG. 1.
Figure 4:
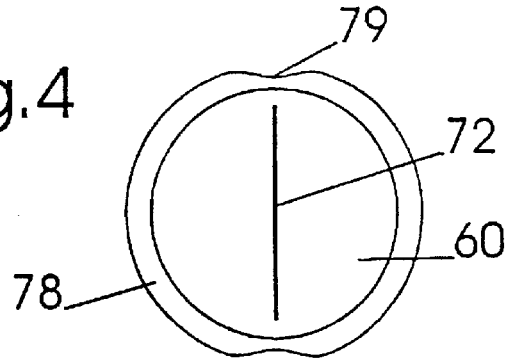
FIG. 4 is a top view of the septum piston in its resting state.
Figure 5:
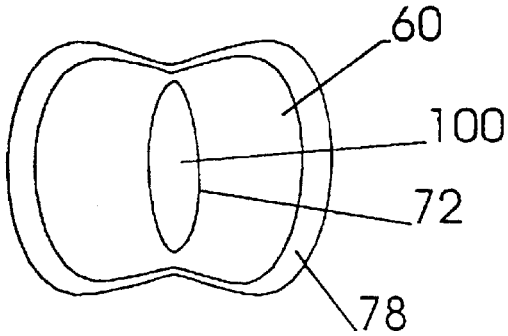
FIG. 5 is a top view of the septum piston in its fully advanced compressed state, showing the open slit.

In one preferred embodiment, the luer tapered cannula receiving valve 5 (FIGS. 1–6) includes a main conduit housing 10 having a main bore 14 and a secondary branch or cylinder 18 having a secondary bore 22. The cylinder 18 includes a distal end 26 adjacent the main bore 10 and a proximal end 30. The cylinder 18 further includes a cylindrical proximal bore portion 34 sized to sealingly receive a conventional tapered luer male cannula 35 (as shown in FIG. 2) and distal bore portion 38. The proximal bore portion 34 is defined by inner cylindrical walls 42 and outer walls 43 and includes outer thread receiving post 44 adjacent the proximal end 30 (although complete outer threads may be provided). A distal bore portion 38 is defined by distal wall 46 having opposing projecting members 50 which effectively narrow the transverse width of the distal bore portion 38 along a longitudinal plane through the opposing projecting members 50 (as best shown in FIG. 3). A cylindrical elastomeric septum piston 60 having a distal end 61 and a proximal end 62 is provided and includes a centrally positioned slit 72 extending from the proximal end 62 to the distal end 61 which can, if desired, receive a steel blunt cannula or sharp needle (not shown). The elastomeric septum piston 60 can be comprised, for example, of silicone rubber or of latex rubber and is both resilient and compressible. The septum piston 60 is preferably sized to be tightly received within the cylindrical proximal bore portion 34 so as to effectively sealingly wipe the cylindrical side walls 42 of the proximal bore portion 34 upon movement of the proximal end 62 of the septum piston 60 back toward the proximal end 30 of the cylinder 18, as will be discussed.

In the preferred embodiment, a silicone lubricant is provided to enhance the sliding piston-like action of the sealingly received septum piston 60 against the side walls 42 and 46 of the cylinder 18. As noted previously, the slit 72 extends completely through the cylindrical septum piston 60. The long transverse axis of the slit 72 (in the transverse plane of the septum piston) is aligned within the same plane as the longitudinal axis through the opposing projecting members 50 of the distal bore portion 38 (FIG. 1 ). Furthermore, the transverse diameter of the distal bore portion along an axis perpendicular to the longitudinal plane of the projecting members 50 can be slightly greater than the transverse diameter of the septum piston 60 to thereby, during operation, receive a bulging portion of the septum piston 60, as will be discussed.

A septum wiper 78 is provided and a bore detent 79 is provided to retain the elastomeric septum piston 60 within the secondary bore by receiving the septum wiper. The wiper 78 is flexible to provide a tight seal. A second wiper (not shown) can be provided adjacent the proximal end 62 to provide additional sealing. The wiper 78 includes a partial recess 79 for receiving the projecting members 50 to allow tight sealing when passing over the members 50. After insertion, during manufacture, the septum wiper 78 engages the detent 80. As shown, the septum wiper 78 is configured so as to allow distal displacement of the septum piston 60 out of its detented position (of FIG. 1), but to prevent proximal bore displacement of the septum piston 60 out of its detented position.

In operation, when a connection, injection, or aspiration is required, a conventional luer taper cannula 35 having a central opening 94 is inserted into the proximal bore portion 34 of the cylinder 18. Advancement of the luer taper cannula 35 causes longitudinal displacement of the septum piston 60 from within the proximal bore portion 34 into the distal bore portion 38 between the projecting portions 50. This causes compression of the septum 60 in an axis which is aligned with the long transverse axis of the longitudinal slit 72 so that the slit 72 is transversely shortened, and thereby opened to define an open fluid flow channel 100. The formerly cylindrical septum piston 60 is narrowed in one transverse axis and bulges and widens in the perpendicular transverse axis, thereby producing an ellipse with a shortened and now opened central slit 72 (FIG. 2 and FIG. 5), although the actual configuration within the cylinder may be limited in situ by the cylinder wall 46. As noted previously, the projecting members 50 progressively enlarge to progressively narrow the width of the distal portion 38 between the projecting members 50. If the elastomer is soft, this will cause the slit 72 to progressively shorten from its proximal extent toward its distal extent and, therefore, the flow channel 100 will be narrower in the proximal extent and wider toward the distal extent. If the elastomer is comprised of a harder elastomer such as high durometer silicone, for example, exceeding 60 durometer-A medical grade, then the slit 72 will be wedged widely open along its entire length.

After the injection or aspiration is complete, the luer taper cannula 35 is withdrawn from the proximal portion 34 of the cylinder 18. Upon removal of the luer taper cannula 35, the septum piston 60 rebounds gently from its formerly advanced position back into its proximal sealing position with the proximal end of the septum piston returning to a position adjacent the proximal end 30 of the cylinder 18. The lubrication of the septum piston 60 and the progressive narrowing of the opposing members 50 causes the resilient septum piston 60 to rebound back from its advanced position. By using a slowly progressive taper, the force of the rebound can be minimized to prevent kickback of the luer 35 from the proximal portion 34 of the cylinder 18. In addition, an umbrella, as will be discussed, could be attached so as to provide less redundancy and, therefore, to provide elastic rebound. As discussed previously, during the return of the septum piston 60 back toward its resting position, the flow channel 100 can progressively close from its proximal extent to its distal extent to effectively express any liquid contained within the flow channel 100 back toward the main bore 10, rather than out toward the cylinder 18.

It can be seen that, by utilizing the achievement of lateral compression by the application of longitudinal displacing force against the septum piston, the rebound force of the septum piston is minimized. In other words, despite the fact that the valve is engaged by longitudinal force of the luer taper, the valve is actually opened by lateral compressive force of the cylinder wall or projecting members, rather than the directly applied activating longitudinal force. Therefore, it is not necessary to have a high resisting longitudinal rebound force to achieve and maintain a tight seal. For this reason, it is not necessary for this valve to utilize a deadspace filler of the type described in my U.S. Pat. No. 5,178,607, as will be discussed later. However, the implementation of deadspace displacement or filler provides an opportunity for utilization in valve, septum piston, or piston configurations wherein deadspace is present and wherein it is desirous to eliminate this deadspace so that recapping is not necessary.

Figure 6:
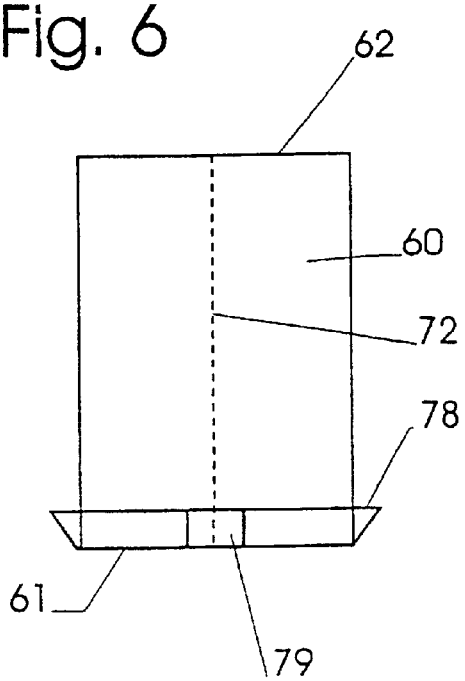
FIG. 6 is a side view of the septum piston of FIG. 1.
Figure 6A:
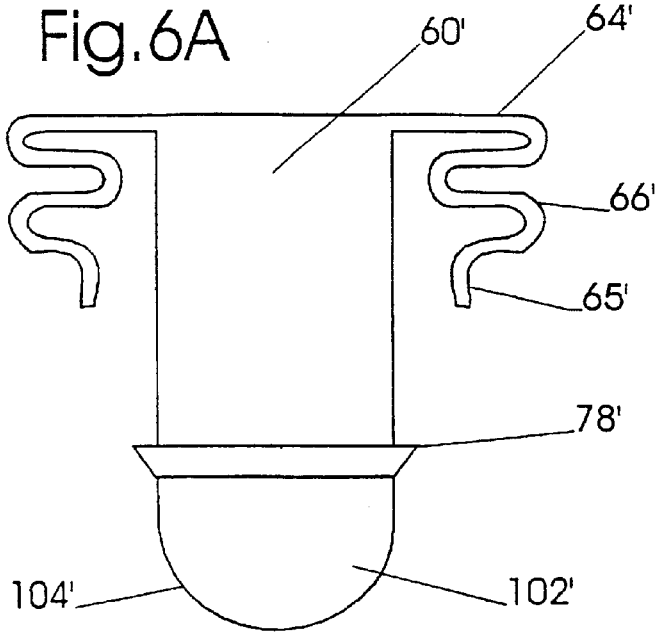
FIG. 6A is a side view of a septum piston having an additional distal portion for occluding the main channel and including a proximal elastic umbrella.
Figure 6B:
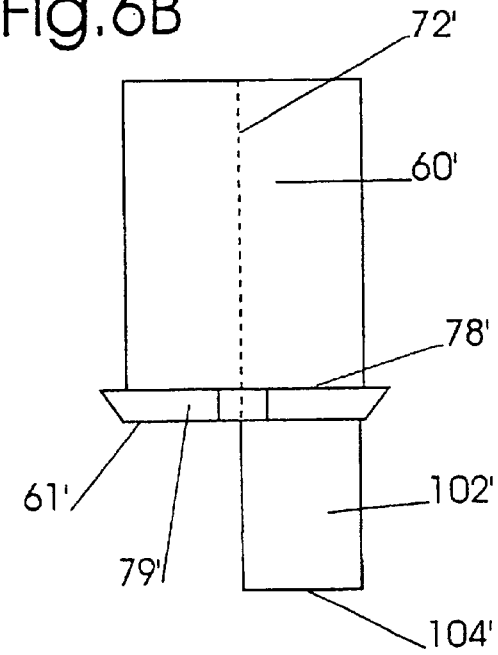
FIG. 6B is a side view of a septum piston showing the distal portion for occluding the main channel.

Another similar septum piston embodiment, as shown in FIG. 6A, the septum piston 60' can include an integral latex or silicone elastic membranous umbrella 64' which can drape over the outer walls 43 and can be bonded or otherwise securely attached to the outer walls 43 along the umbrella end 65' when the septum piston 60' is inserted into the proximal bore portion 34. This prevents any potential opening at proximal end 30 adjacent inner walls 42 and septum piston 60'. A redundant or bulging umbrella portion 66' may be provided and the umbrella attached distally to allow the redundant portion 66' to be free and to allow less inhibition of longitudinal displacement of the integral septum piston 60' into the distal bore portion 38 during operation.

Figure 6C:
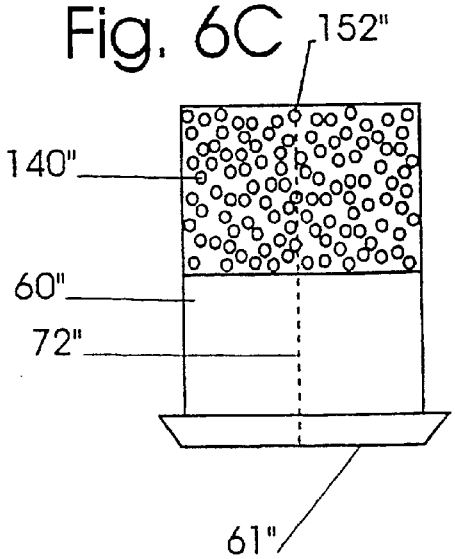
FIG. 6C is another embodiment showing the proximal soft and compressible deadspace filler in association with the septum piston.

In one septum piston embodiment (FIGS. 6A and 6C), a projecting main bore occluding member 102' is provided adjacent the distal end of the septum piston 60'. The occluding member 102' includes a circular distal end 104' and is sized to be sealingly received into the main bore 10 when the septum piston 60' is advanced. For operation of this embodiment, the cylinder 18 is preferably positioned at an angle relative to the main housing 10 and the secondary bore 22 intersects the main bore 10 at an angle which may be 30°–90° (as in FIG. 1 ). The main bore 10 is connected distally to a distal conduit which is in fluid connection with a patient's blood vessel. The main bore 10 is connected proximally to a proximal conduit which is in fluid connection with a primary fluid source, such as a high pressure flush bag or a bag of intravenous fluid. The operation of this embodiment is similar to the aforementioned embodiment; however, the occluding member 102' extends distally upon advancement of the septum piston 60' so that the occluding member 102' passes the flow deflector 110' and occludes the main bore 10 adjacent the cylinder 18 in a position intermediate the cylinder 18 and the primary fluid source. This embodiment provides closure of fluid connection between the secondary bore 22 and the primary fluid source, as well as between the patient and the primary fluid source during either aspiration or injection of fluid from the secondary bore 22. This embodiment, therefore, functions to open communication between the opening 94 of the luer 35 and the patient through the septum piston 60' and the main bore 10, while at the same time automatically occluding fluid communication between the primary fluid source and the patient, as well as occluding communication between the primary fluid source and the opening 94 of the luer cannula 35. During injection, this automatically prevents reflux of fluid upstream toward the primary fluid source and assures that the injected fluid is injected toward the patient. During aspiration, this assures that fluid will come from the patient and not from the primary fluid source. The flow deflector 110 can also be sized so that it is engaged by the distal end 61' of the septum piston 60' to prevent excessive advancement of septum piston 60', thereby also functioning as a septum piston stop.

In another embodiment (FIG. 6C), the septum piston 60" is shorter and a soft deadspace filler 140" is provided. The deadspace filler can be of the type and design for use with very blunt cannulae as discussed in my U.S. Pat. No. 5,178,607 (the disclosure of which is hereby incorporated by reference as if completely disclosed herein). The soft outer filler 140" serves to minimize kickback of the luer taper cannula 35 and functions as a deadspace occluder or displacer. The soft filler 140" can be comprised of foam rubber which can be covered by a medical grade silicone of the type similar to that used in foam cuffs sold by the Bavona Corporation for tracheostomy tubes or can be otherwise constructed to have a similar ease compressibility and relatively low volume in the compressed state and high volume in the resting non-compressed state. The soft portion 140" provides a central perforation 152" for receiving the luer taper cannula 35 through the portion 140" and subsequently into contact with the less easily compressible septum piston 60". Although it is preferred that the two portions be bonded together, they may be separate and the proximal portion may be bonded to the proximal inner walls 42 or the cylinder end 30 or may include an umbrella of the type shown in FIG. 6A or may include another attaching member. As can be seen, the outer soft, easily displaceable filler 140" functions as a deadspace displacer to allow receipt of an extremely blunt cannula, such as a luer taper cannula 35, into a fixed position in relationship with a more stiff and less compressible valve or septum piston 60", the septum piston 60" functions as the actual valve to provide a tight seal and to prevent leakage of even high pressure fluid within the main bore 10. It is the combination of a soft, easily compressible and displaceable outer member 140" in association with a tight sealing lower septum piston or valve 60" which achieves the ability to splint a luer taper cannula 35 in position for reliable engagement with the actual valve mechanism 60", while at the same time allowing for the elimination of deadspace by the soft, easily compressible outer member 140".

Figure 7:
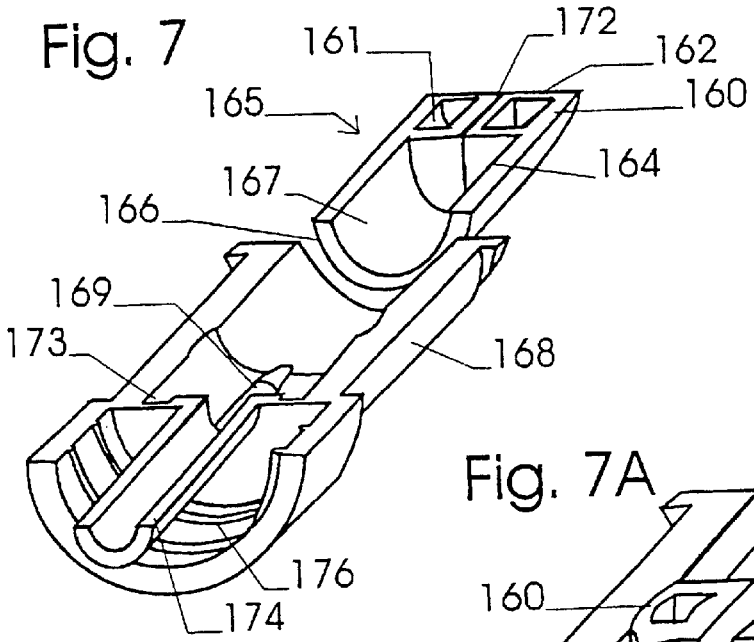
FIG. 7 is an exploded perspective view of a longitudinal section of a valve having a flexible seated conduit.
Figure 7A:
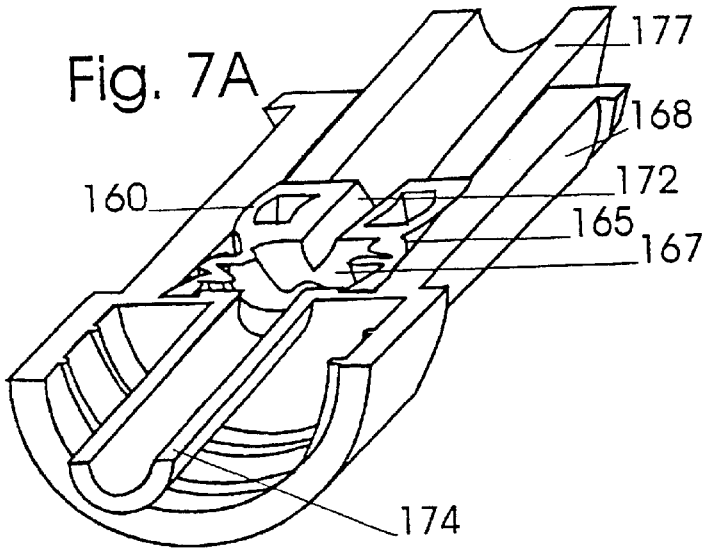
FIG. 7A is a perspective view of a longitudinal section, according to FIG. 7, with the proximal end of the conduit displaced into the distal position and the perforation biased into an open position.
Figure 8:
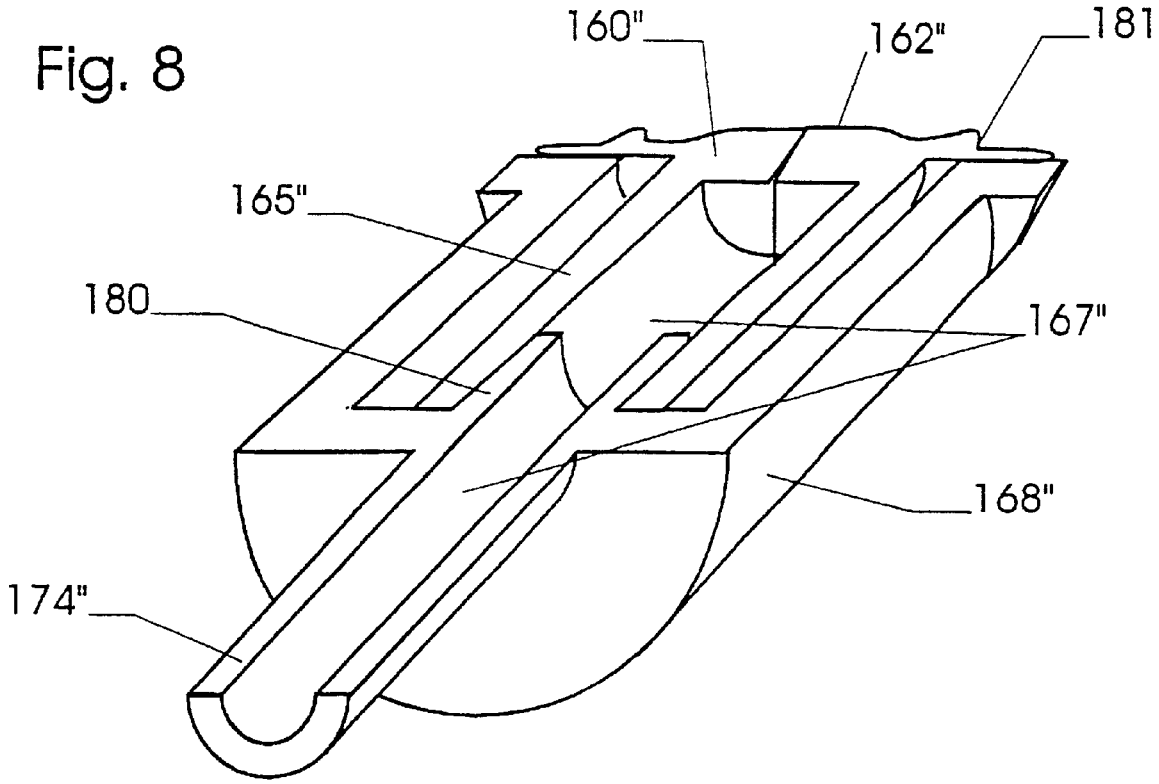
FIG. 8 is a perspective view of a longitudinal section showing an elongated septum piston.
Figure 9:
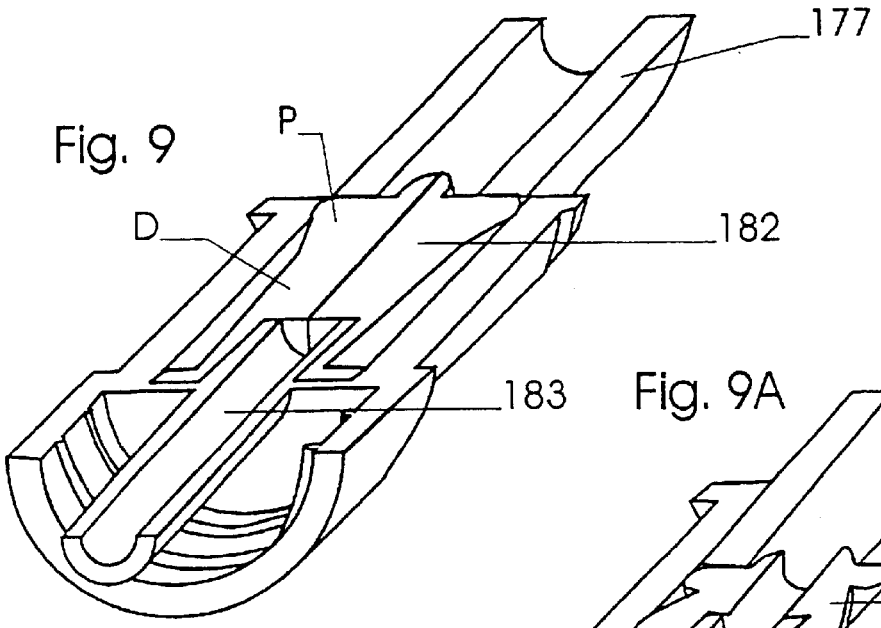
FIG. 9 is a perspective view of a longitudinal section of an embodiment having an elongated septum.

Alternative septum and housing configurations are shown in FIGS. 7 through 9. FIG. 7 is an exploded view of one preferred embodiment showing an elastomeric septum piston 160 having cavities 161 to increase flexibility of piston 160 and having an upper face 162, slit 172, and including integral elastomeric tubular extension 164 defining a flexible tubular conduit 165 having an open distal end 166 and defining an interior flow path or lumen 167. The flexible conduit is received into a cylindrical housing 168. Opposing projecting members 169 are provided along cylindrical housing 168 to bias the septum 160 and to achieve distortion and opening of slit 172, as described for the previous embodiments. The projecting member 169 can be triangular in cross-section or frustrum-shaped with a narrow apex focused directly toward the long transverse axis of slit 172 so that maximum shortening can occur with minimum frictional and compressive resistance to advancement of the septum. Seats 173 are provided to receive the distal end 166 of conduit 165. Rigid tube 174 is provided for fluid communication between flow path 167 of flexible conduit 165 and the primary tubing system (not shown) such as a catheter connected to a patient's vein. A female threadable member 176 is provided for attachment to the primary system, as discussed previously. FIG. 7A illustrates operation of the embodiment of FIG. 7. The flexible conduit extension 165 is compressed as the septum piston 160 is advanced along the housing 168 by luer tip 177. Transverse compression or distortion of septum piston 160 by projecting members 169 induces opening of slit 172. The compression or folding of resilient conduit 165 provides for additional rebound of septum 160 toward its original resting position once the luer tip 177 is removed. The flexible conduit 165 in tight sealed connection adjacent rigid tube 174 provides a closed flow path 167 to prevent contamination of fluid passing through open slit 172.

Figure 7B:
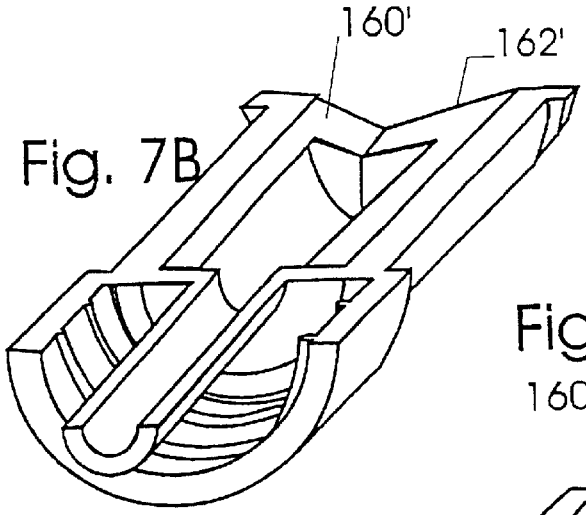
FIG. 7B is a perspective view of a longitudinal section showing a modified flexible conduit having a tapered outer face.
Figure 7C:
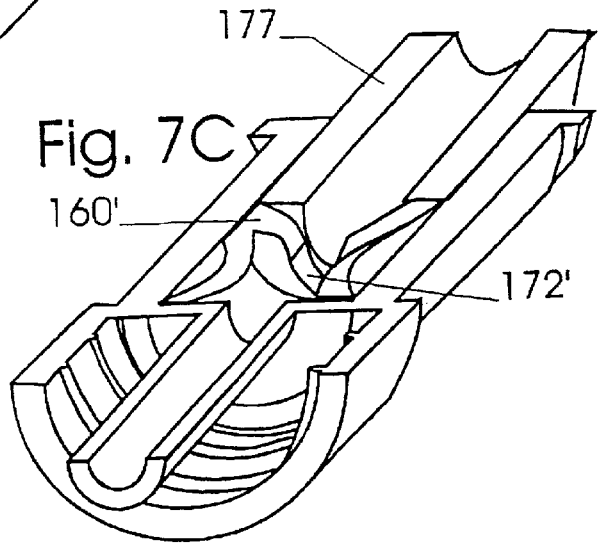
FIG. 7C is a perspective view of a longitudinal section, according to FIG. 7B, showing the proximal end of the flexible conduit displaced into the distal position with the slit biased into an open position.

FIG. 7B illustrates an embodiment similar to FIG. 7 with a more thin septum piston 160' which can be more easily opened by lateral compression. The septum piston 160' has an inwardly tapering outer face 162'. This outer face deflects inwardly in the direction of the longitudinal force of the advancing luer tip 177, thereby facilitating opening of the slit 172', as shown in FIG. 7C.

FIG. 8 shows one preferred embodiment with a rigid tubular seat 180 which comprises an extension of tube 174", thereby providing a continuous flow path 167" between the flexible conduit 165" and the rigid tube 180. The septum piston 160" includes transverse membranous apron extension 181 which is deflected inwardly on displacement of the septum piston 160" into cylinder housing 168" by the luer end 177. Apron 181 thereby facilitates circumferential sealing of the luer tip 177 when the luer tip 177 is advanced against septum piston face 162".

Figure 9A:
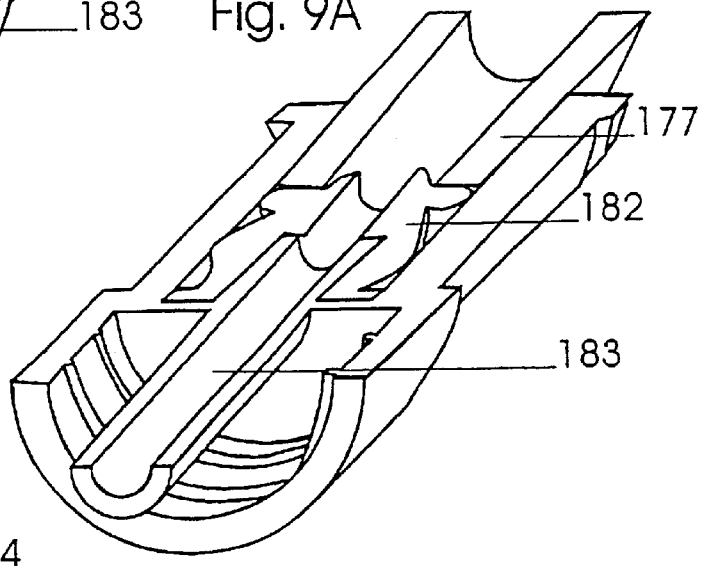
FIG. 9A is a perspective view of a longitudinal section, according to FIG. 9, with the occluding piston displaced such that the slit is distorted into the open position.
Figure 9C:
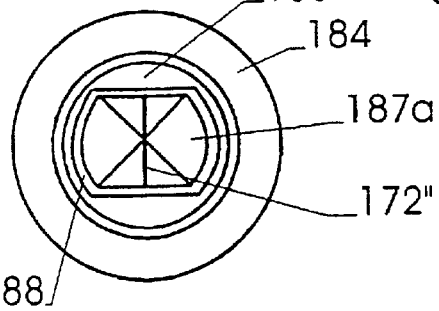
FIG. 9C is a transverse section through lines 9C—9C of FIG. 9B.
Figure 9B:
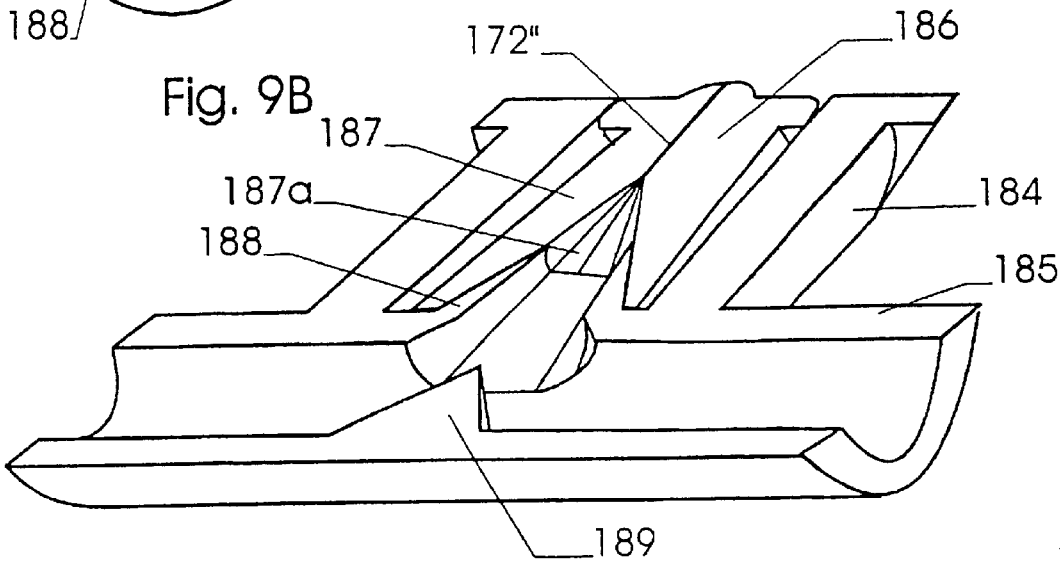
FIG. 9B is a longitudinal section view of an embodiment having a flow deflector and a wedge-shaped tubular seat.

FIGS. 9 and 9A disclose an embodiment having a longer septum piston 182. This reduces the potential for deadspace and therefore minimizes the potential for negative pressure to develop within flow channel 183 during rebound of the piston 182 from its open position of FIG. 9A to its closed position of FIG. 9. FIG. 9B shows housing support 184 carried by primary tubing system 185. Septum piston 186 is provided integral with flexible conduit 187 and comprises the occluding proximal end of the flexible conduit. The flexible conduit 187 is intussuscepted over and seated with tubular wedge-shaped seat 188. A fluid deflector or ramp 189 is provided, which can deflect fluid travelling through primary tubing system 185 into tubular seat 188 to flush out trapped air or blood adjacent septum 186. The operation and rationale for fluid deflection in association with blood aspiration systems is discussed in my U.S. Pat. No. 5,137,524.

FIG. 9 shows the longer septum piston 182 having a greater diameter in proximal area P than in distal area D. FIG. 9A illustrates lateral compression against area P to distort the septum piston 182 into the open configuration. The embodiment of FIG. 9B uses combined forces of lateral compression, as previously described, and the wedge force induced by progressive compressive and/or displacing intussusception over wedge-shaped rigid tube 188. (This is in contradistinction to the embodiment of FIG. 7C where the wedge effect of the luer taper is combined with lateral compression or distortion to open the slit and allow the luer to penetrate the slit.) With such downward displacement, the wedge force is applied against inner walls 187a transverse to the longitudinal axis of septum 186. This force is synergistic with the force induced by the distorting protruding member (not visible in this figure, but shown with previous embodiments, as 50 and 169) of housing 184 to effectively split open the slit 172".

Figure 11:
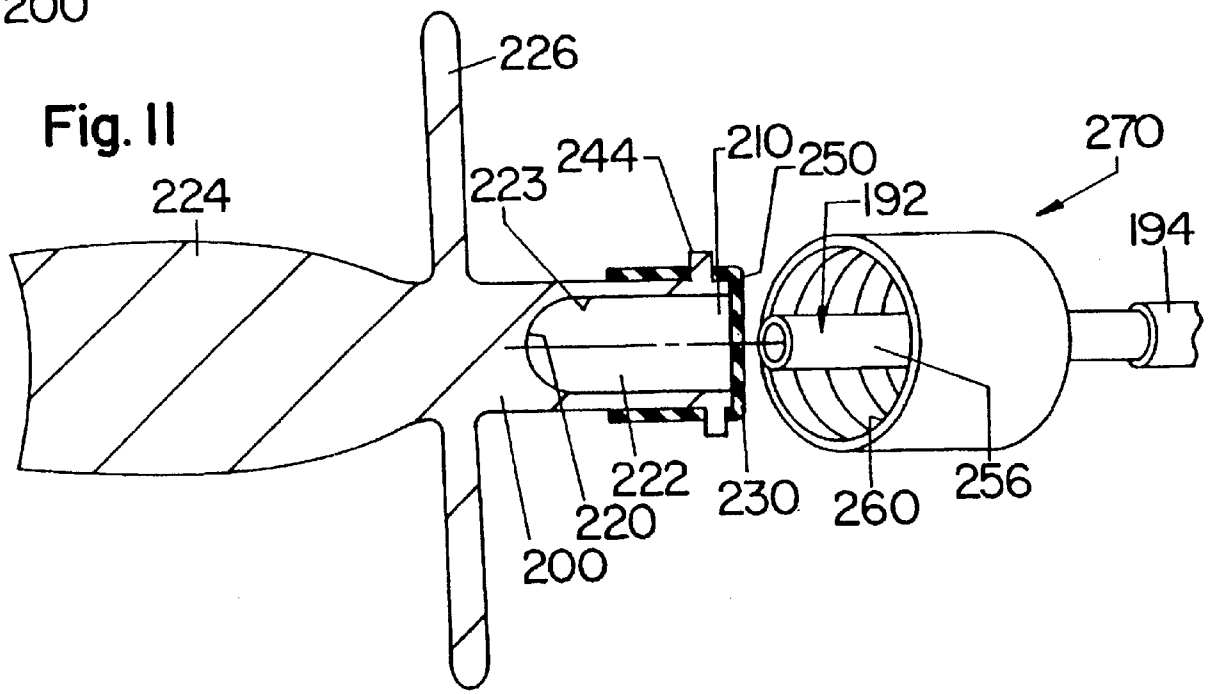
FIG. 11 is a longitudinal section view of a luer tapered cannula protection station showing an adjacent conventional luer lock connector.
Figure 12:
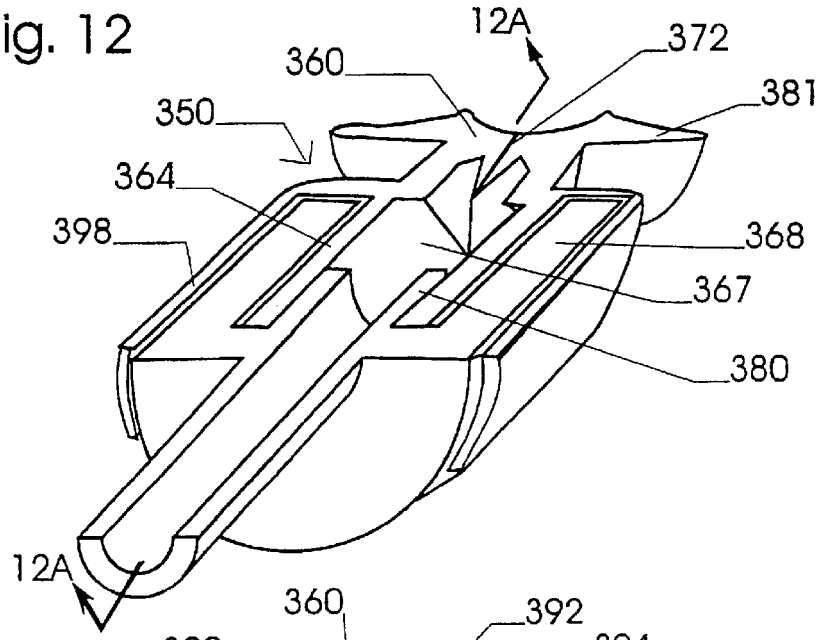
FIG. 12 is a perspective view of a longitudinal section of an embodiment having opposing supporting bars and intervening slots adjacent the septum.

FIG. 12 illustrates an embodiment which combines some of the features of FIG. 7C with those of FIG. 8 and includes additional features, as will be discussed. The embodiment, as illustrated, includes a septum 360 which is generally rectangular in cross-section and which can function as a piston and/or can receive a luer tip 177 into the septum 360, as will be discussed. The septum 360 includes a slit 372, an apron or umbrella 381, and a proximally projecting flexible conduit 364 defining a lumen 367. Support housing 368 is provided, which includes projecting supporting bars 369 having an outer flange 370 for receiving a female threaded member of the type shown in FIG. 11. Septum 360 includes an outer deflecting member 390. Longitudinal displacement of the septum 360 against the bars 369 causes lateral compression force (as illustrated by arrows in FIG. 12C) against the deflecting members 390, thereby facilitating opening of the proximal end 373 (as illustrated in FIGS. 12D through 12E). Although rounded deflecting members 390 are shown, they may be frustrum-shaped or triangular in cross-section to more focus the compressive force toward slit 372.

As shown in FIG. 12 and FIG. 12C, septum 360 may include strap members 398 extending through slots 350 to position septum 360 relative to the inlet and secure it with respect thereto.

Figure 12A:
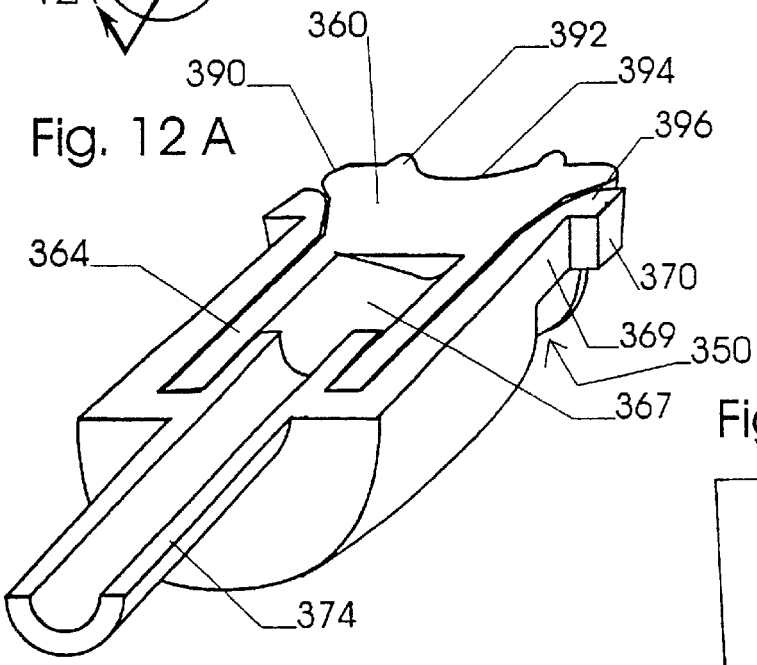
FIG. 12A is a perspective view of a longitudinal section through the slit along lines 12A—12A of FIG. 12.
Figure 12B:
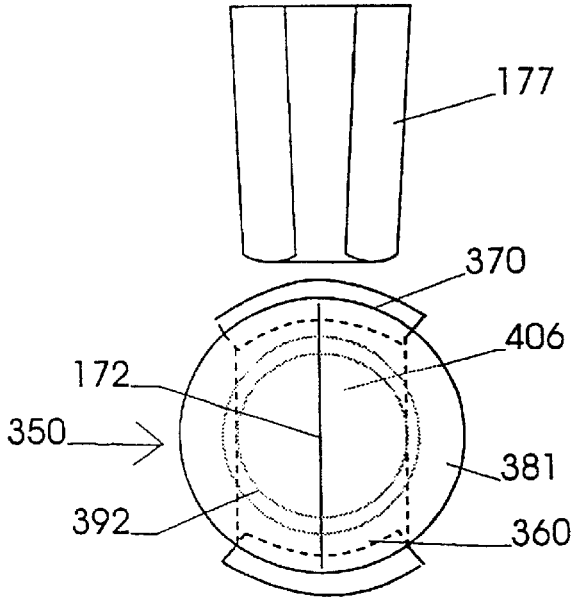
FIG. 12B is a partial top view of the embodiment of FIG. 12 and FIG. 12A, illustrating the relationship of the conventional male luer end to the septum face.

In the preferred embodiment, the slit 372 in the resting state has a length which is approximately equal or slightly greater than the diameter of a conventional lure taper 177. As shown in FIG. 12D, the transverse section of the septum defines a nearly rectangular or elongated ellipsoid structure with the slit 372 extending centrally along the major axis (M). The slit 372 is nearly equal in length to the length of the major axis and is approximately equal or slightly greater in length the diameter of the tip of the luer taper 177. The slit divides the septum into thick walls 406 and thin walls 400. FIG. 12E illustrates the effect of the insertion of a luer taper 177 into the slit 372 (note that a new ellipsoid structure is derived, having a major axis M' perpendicular to the major axis M of the original ellipsoid septum of FIG. 12D). This outward deflection of lateral walls 406 is accommodated by slots 350 between opposing supports 369 (see FIG. 12A); therefore, substantial increase in the cross-sectional area of the septum 360 when filled with luer tip 177 is accommodated by deflection of a major portion of the mass of septum 360 into slots 350, thereby allowing fixed and narrow separation of supports 396 and flanges 370 so that opposing flanges 370 may maintain a suitable spatial relationship for receipt of the female threaded member of a conventional luer lock connector. The septum 360 includes annular elevation 392 to provide a target for male luer tip 177. An angled recess 394 is provided to facilitate wedge opening of the slit 372 by the luer taper 177. It can be seen that the wedge effect of the luer tip 177 engaging the recess 394 is combined with the compressive deflection force of the projecting members 369 to provide synergistic forces to open slit 372. The diameter of the tip of a conventional male luer end 177 is approximately 3.5–4 mm. The internal diameter of the female threaded luer lock connector (as shown in FIG. 11) is approximately 7–8 mm. The width of each of the lateral walls 406 can be, for example, 1–2 mm. The distance between the opposing flanges 370 can be, for example, 7–8 mm so that the conventional female threaded member can be received over and locked with the flanges 370.

It should be clear that alternative configurations of the septum piston are possible within the scope of the present invention. These configurations result in enhanced opening of the slit and minimize the volume of the septum so that adequate clearance is provided to allow insertion into septum the within the spatial limitations defined by a conventional female threading member of a luer lock connector. The septum piston could be otherwise distorted, either longitudinally or horizontally, in association with longitudinal displacement to achieve an open fluid path. It is, however, preferable that this open fluid path extend through the septum piston and directly in contact with the bore of the luer taper cannula so as to facilitate flow and to absolutely minimize the trapping of fluid or blood within the valve.

Figure 10:
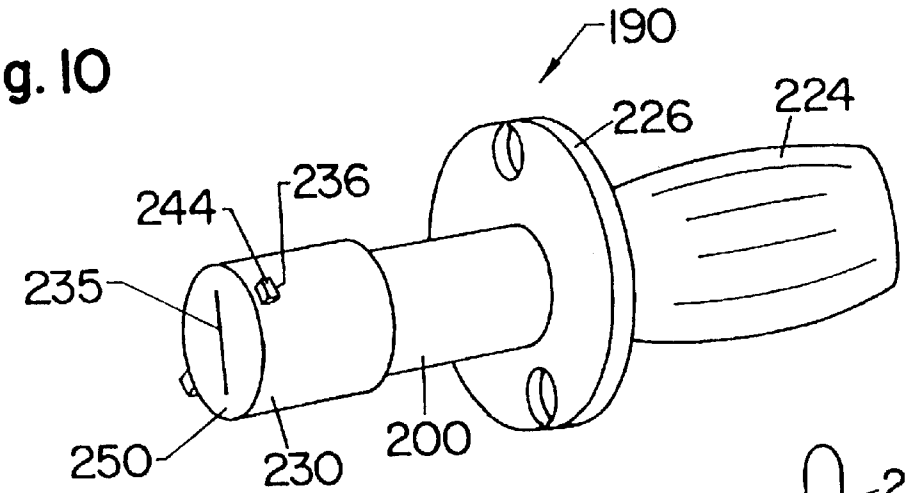
FIG. 10 is a perspective view of a luer tapered cannula protection station.

FIG. 10 shows a luer taper protecting station 190, which is intended to protect the blunt tapered luer cannula 192 connected to a secondary IV piggyback tubing system 194. The station 190 includes a housing 200 having an open distal end 210 and a closed end 220 defining a chamber 222 having a bore 223. The closed end 220 preferably includes a handle rod 224 and connecting or shield portion 226 for connection to an IV piggyback tubing or the protection station 190 may be otherwise connected along the piggyback system or the pole holding the piggyback system so as to allow easy storage, as discussed in my aforementioned patent. In the preferred embodiment, the open end 210 is occluded by an elastomeric boot 230 which has a closed longitudinal slit 235. The boot is preferably of thin membranous elastomeric material, such as latex rubber or silicone and may be bonded to the housing 200 or otherwise secured. An opening 236 in boot 230 is preferably provided to receive the thread receiving post 244 which is tall enough to threadably engage with the female threading member which is carried by a conventional luer lock connector without disruption of the boot 230. If necessary to prevent the threads of the luer lock from potentially disrupting the boot during threading, two tall posts may be provided on opposite sides of the housing 200. The boot 230, when attached to the distal end of the station 190, produces a distal face 250 which is easily swabbable with antiseptic. As noted, the boot 230 material is preferably membranous elastic and resilient so that, despite the fact that the male luer taper 192 is close in diameter to the internal transverse dimension of the bore of the station, the elastic boot can be deflected laterally against the inner walls 254 of the station 190 so that even the large diameter of a luer taper 192 can be received within the bore 223 of the station 190 without being inhibited by the low displacement volume and, indeed, easily displaceable elastic boot 230. This is an important feature since there is relatively little clearance between the outer surface 256 of a conventional male tapered luer cannula 192 and the inner surface 260 of the threadable luer lock connector 270 surrounding the taper 192 which must be received over the station 190. It is, therefore, important that the sealing member has a very low displacement or compressed volume so that luer lock connector 270 may be fully received over and through the boot 230 and into the station 190 without the advancement of the cannula 192 fully into the bore 222 being inhibited by the displaced face 250 of boot 230.

Although an elastic membranous boot is shown, a perforated deadspace filler, of the type previously discussed with a compressed low displacement volume, may be used to fill the bore of the station and to receive and cover the luer taper.

Although the presently preferred embodiments of this invention have been described, it will be obvious to those skilled in the an that various changes and modifications may be made therein without departing from the invention. Therefore, the claims are intended to include all such changes and modifications which may be made therein without departing from the invention. Therefore, the claims are intended to include all such changes and modifications that fall within the true spirit and scope of the invention.

I claim:

1. A medical luer receiver for the sterile transfer of fluid from a luer-tapered male end having a surrounding female luer lock threaded end, comprising:

a. a housing having an inlet and an outlet and a lumen extending from said inlet to said outlet;

b. an elastomeric sealing member defining a longitudinal axis and having a central portion and occluding said inlet, said sealing member having an outerface;

c. a slit extending through said sealing member, said slit defining a long transverse axis transverse to said longitudinal axis, and further having a length along said long transverse axis sufficient to receive said male end into said slit;

d. a support portion defining a longitudinal axis, said support portion being positioned adjacent said inlet and adjacent said sealing member;

e. said support portion including opposing posts and slots defined therebetween, said slots functioning to allow expansion of said sealing member when said male end is inserted into said slit.

2. The receiver of claim 1 wherein said sealing member defines an elongated cross-section transverse said sealing member longitudinal axis, said sealing member defining opposing lateral walls adjacent said long transverse axis of said slit.

3. The receiver of claim 2 wherein said slots are positioned adjacent said sealing member such that said lateral walls are deflected into said slots when said male end is received into said slit of said sealing member.

4. A medical connection system for the sterile transfer of fluid, comprising:

a. a luer-lock connector including an open female cylindrical end, said end defining an interior threaded wall, said connector further including a cannula centrally positioned within said cylindrical female end, said wall and said cannula defining a partially enclosed narrow tubular space intermediate said cannula and said wall, b. a connection terminal including a housing having an inlet and an outlet, said housing adjacent said inlet being sized to be received within said tubular space, c. an elastomeric sealing member mounted within said inlet, said member defining a longitudinal axis, said member further defining a proximal end portion adjacent said inlet, said proximal end portion including an outer face, d. a perforation extending through said sealing member, at least a portion of said perforation being capable of receiving at least a portion of said cannula by penetration of said cannula into said perforation, said cannula upon said penetration displacing at least a portion of said sealing member transverse to said axis to define a displaced member, e. said housing having at least one cutout adjacent said inlet, said cutout functioning to receive at least a portion of said displaced member into said tubular space when said cannula is received into said perforation so that said housing adjacent said inlet and at least said proximal end portion of said sealing member can be received into said female cylindrical end when said cannula is received into said perforation.

5. The system of claim 4 wherein said housing adjacent said inlet includes at least one flange for engaging said threaded wall so that said female cylindrical end can be threaded onto said housing to securely connect said female end to said housing.

6. The system of claim 4 wherein said housing includes at least one cantilevered bar adjacent said inlet sized for being received within said tubular space of said female end.

7. The system of claim 6 wherein at least two directly opposed cantilevered bars are provided adjacent said inlet.

8. The system of claim 7 wherein said bars define slots intermediate said bars for receiving said displaced member of said sealing member.

9. The system of claim 8 wherein said bars are directly opposed, said sealing member being mounted intermediate said directly opposed bars.

10. The system of claim 9 wherein said perforation is a slit.

11. The system of claim 10 wherein said slit is aligned with said bars such that said slit extends from adjacent one said bar to a position adjacent the bar opposing said one bar.

12. A medical connection terminal for secure connection of a luer lock connector having a female threaded end, said connector having a cannula centrally disposed within said female end, the terminal comprising:

a. a rigid housing defining an axis and having a proximal portion and a distal portion, said housing having an inlet adjacent said proximal portion and an outlet adjacent said distal portion, said proximal portion having at least one cutout adjacent said inlet, b. an elastomeric sealing member mounted within said inlet, said member having an outer face and a sealed perforation extending through said member from adjacent said outer face toward said outlet, said perforation being sized to receive said cannula, said member expanding adjacent said outer face to define an expanded sealing member when said cannula is received within said perforation, at least a portion of said expanded member expanding into said cutout, said expanded member and said proximal portion of said housing being sized to be threadably received within said female end so that when said cannula is inserted into said perforation, said female end can be threadably locked over said proximal portion of said housing.

13. A medical connection terminal of claim 12 wherein said proximal portion of said housing includes at least two cutouts.

14. The medical connection terminal of claim 13 wherein said cutouts are oppositely disposed, said housing further including at least two oppositely disposed cantilevered bars intermediate said cutouts.

15. The medical connection terminal of claim 14 wherein said perforation is a slit.

16. The medical connection terminal of claim 15 wherein said sealing member defines a longitudinal axis and wherein said slit defines a longitudinal axis transverse to said sealing member longitudinal axis, said slit dividing said sealing member into oppositely disposed lateral portions, said longitudinal axis of said slit being aligned with said bars so that when said cannula is received into said slit, said oppositely disposed lateral portions are displaced by said cannula into said cutouts.

17. The medical connection terminal of claim 16 wherein said sealing member includes a proximal portion and a distal portion, said proximal portion of said sealing member having an elongated cross-section defining a major axis, said longitudinal axis of said slit extending along said major axis.

18. The medical connection terminal of claim 17 wherein said proximal portion of said sealing member is more compliant than said distal portion.

19. The medical connection terminal of claim 12 further including at least one strap member connected to said sealing member, said strap member extending through said cutout, said strap member functioning to secure said sealing member to said housing in said mounted position within said inlet.

20. A medical luer lock connection system comprising:

a. a male connection terminal defining a rigid housing having *a longitudinal axis,* an inlet*, an outlet, and a lumen extending along said axis,* and an elastomeric sealing member mounted within said inlet, *said elastomeric sealing member comprising an elastomeric upper portion and a vertically extending elastomeric lower portion integral with said upper portion, said elastomeric lower portion projection downwardly from said elastomeric upper portion along said longitudinal axis of said housing, said lumen providing an open flow path from said elastomeric lower portion through said housing to said outlet,* b. a cylindrical female connection terminal including cylindrical interior walls, said interior walls including a locking member for locking onto said rigid housing, said female terminal having a centrally disposed blunt cannula projecting therein, said female terminal defining a narrow tubular open space intermediate said central cannula and said interior walls, said female terminal being sized to be received over said housing adjacent said inlet, c. a sealed perforation through said elastomeric sealing member for receiving said cannula, *said perforation comprising a slit, said slit having a first length, transverse to said longitudinal axis, that is sufficient to receive said central cannula into said slit, said slit having a second length generally along said longitudinal axis through said upper portion, and through said vertically extending lower portion, to substantially divide said lower portion into opposing lateral elastomeric wall portions, said wall portions contacting each other to seal said slit,* d. said housing including a proximal portion adjacent said inlet, said proximal portion including oppositely disposed slots, said proximal portion of said housing further being sized to be received within said tubular open space of said female connection terminal, *said opposing lateral elastomeric wall portions being positioned adjacent said oppositely disposed slots such that said opposing lateral elastomeric wall portions define inner peripheries of said slots,* e. said blunt cannula displacing at least a portion of said elastomeric sealing member into said slots when said cannula is received into said perforation to define a displaced member, said slots *thus* functioning to receive at least a portion of said displaced member, f. said proximal portion of said housing, and at least a portion of said displaced member within said slots being received into said narrow space when said cannula is received into said perforation and said female connection terminal is locked onto said housing of said male connection terminal.

21. The connection system of claim 20 wherein said narrow tubular open space is approximately 3 mm or less in width.

22. The connection system of claim 21 wherein said cannula has an approximate diameter of [3–4] *3.5–4* mm.

23. The connection system of claim 22 wherein said female connection terminal has an internal diameter intermediate said interior walls of approximately 7–8 mm.

24. The connection system of claim 23 wherein said perforation is a slit having a length approximately equal to the diameter of said cannula.

25. A medical connection system comprising:

a. a first terminal including a luer lock connector, said connector having a cylindrical female end and a blunt cannula centrally disposed within said end, b. a second terminal including a housing having an inlet and an outlet and defining a housing portion adjacent said inlet, said portion including at least one cutout, said housing portion being sized to be received into said female end of said first terminal, c. an elastomeric sealing member disposed within said inlet of said second terminal, said member having an outer face and being mounted with said second terminal such that said outer face is adjacent said inlet, said sealing member having a perforation extending from said outer face through said sealing member for receiving said cannula, said sealing member, and said cutout being configured such that said sealing member can expand into said cutout when said cannula is inserted into said perforation, said housing portion with said sealing member being sized so as to be received into said female end when said cannula is received into said perforation and said sealing member has expanded into said cutout.

26. A connection system for connecting a first tubing system with a second tubing system, said system including:

a. a female terminal comprising a cylindrical female luer lock connector defining interior threaded walls and having a cannula centrally disposed within said connector, b. a male terminal comprising a rigid housing defining an axis and having a proximal portion including an inlet and a distal portion including an outlet, said proximal portion having opposing cantilevered bars and further having opposing slots intermediate said bars, said bars including at least one flange, said bars being sized to be received within said female luer lock connector such that said flange can engage said interior threaded walls, c. an elastomeric sealing member mounted within said inlet and having a closed central perforation through said member, said perforation being sized to receive said cannula, at least a portion of said sealing member deflecting upon receipt of said cannula into said perforation to define at least one deflected sealing member portion, said sealing member, said bars, and said cutouts being sized and configured so that said bars and said sealing member can be received into said female luer lock connector when said cannula is advanced into said perforation so that said female luer lock connector may be threadably locked about said proximal portion when said centrally positioned cannula is received within said perforation.

*27. The connection system of claim 20, wherein said elastomeric upper portion of said sealing member defines an elastomeric umbrella that covers said inlet, said umbrella having an upper surface and being mounted to said housing such that said outer surface is disposed adjacent said inlet, said elastomeric lower portion of said sealing member projects downwardly from said umbrella along said longitudinal axis of said housing, said elastomeric lower portion defining, in transverse cross-section, a nearly rectangular or elongated ellipsoid structure having a major axis transverse to said longitudinal axis of said housing and a major axis perpendicular to said major axis, said first length of said slit is generally aligned with said major axis of said lower portion, said cylindrical female connection terminal comprises a luer lock connector, and said blunt cannula comprises a luer cannula having a luer tip.*

*28. The connection system of claim 27 wherein said vertically extending lower portion has a length along said major axis greater than said first length of said slit so that said lower portion defines end walls at the ends of the slit.*

*29. The connection system of claim 28 wherein a deflection of said lateral elastomeric wall portions along said minor axis when said luer tip is advanced into said slit is greater then a deflection of said end elastomeric walls along said major axis when said luer tip is advanced into said slit.*

*30. The connection system of claim 28 wherein a length of said lower portion along said major axis is less when said luer tip is advanced into said slit through said lower portion than when the slit is free from said luer tip, said end walls moving closer together when said luer tip is advanced into said slit to tightly seal about said luer tip.*

*31. The connection system of claim 27 wherein said elastomeric umbrella defines an upper wall of each of said oppositely disposed slots.*

*32. The connection system of claim 27 wherein a length of said lower portion along said minor axis is greater when said luer tip is advanced into said slit through said extension than when the slit is free from said luer tip.*

*33. The connection system of claim 27 wherein a length of said lower portion along said minor axis in at least one cross-sectional plane through said lower portion is about 2 mm when said slit is free from penetration by said luer tip.*

*34. The connection system of claim 27 wherein a length of said lower portion along said minor axis in at least one cross-sectional plane through said lower portion falls within a range of about 2 mm–4 mm when said slit is free from penetration by said luer tip.*

*35. The connection system of claim 34 wherein the length of said lower portion along said minor axis in said at least one cross-sectional plane through said lower portion falls within a range of about 5.5–8 mm when the luer tip is positioned within said slit of said lower portion.*

*36. The connection system of claim 20 wherein said proximal portion of said housing is defined by a peripheral wall adjacent said inlet, said slots extending into said peripheral wall as cutouts.*

*37. The connection system of claim 20 wherein said lateral wall portions are about 1 mm in thickness.*

*38. The connection system of claim 37 wherein when the luer tip is positioned within said slit of said lower portion, a combined dimension of said lower portion along said major axis and a dimension of said lower portion along said minor axis is approximately 1.0–2.5 mm less than a corresponding internal diameter of the female luer lock connector.*

*39. The connection system of claim 20 wherein a dimension of said lower portion in a direction transverse to said first length of said slit in at least one cross-sectional plane through said lower portion is about 2 mm when said slit is free from penetration by said luer tip.*

*40. The connection system of claim 39 wherein a dimension of said lower portion in a direction transverse to said first length of said slit in said at least one cross-sectional plane through said lower portion is about 5.5 mm when the luer tip is positioned within said slit in said lower portion.*

*41. The connection system of claim 20 wherein said elastomeric sealing member further includes an elastomeric tubular extension mounted within said lumen and projecting from said lower portion, said extension defining an internal flow path in fluid communication with said outlet, said extension isolating said flow path from fluid communication with said housing.*

*42. The connection system of claim 41 further including a rigid tube projecting within said housing toward said inlet, said tube defining a bore, said extension being mounted about said tube, so that said bore is in fluid communication with said flow path of said extension and further in fluid communication with said lower portion of said elastomeric sealing member.*

*43. The connection system of claim 42 wherein said elastomeric extension is intussuscepted over said tube.*

*44. The connection system of claim 20 wherein said oppositely disposed slots are in parallel alignment with a plane of said slit.*

*45. The connection system of claim 20 wherein said oppositely disposed slots are transversely separated from each other by said opposing elastomeric lateral wall portions of said lower portion.*

*46. The connection system of claim 45 wherein said slots are transversely separated by about 2 mm.*

*47. The connection system of claim 20 wherein the housing and the lower portion of the elastomeric sealing member define said slots therebetween for receiving at least a portion of the lower portion of the elastomeric sealing member when the central cannula is inserted into the housing.*

* * * * *